Nov. 25, 1958 S. REECE ET AL Plant Pat. 1,774
ROSE PLANT
Filed April 21, 1958
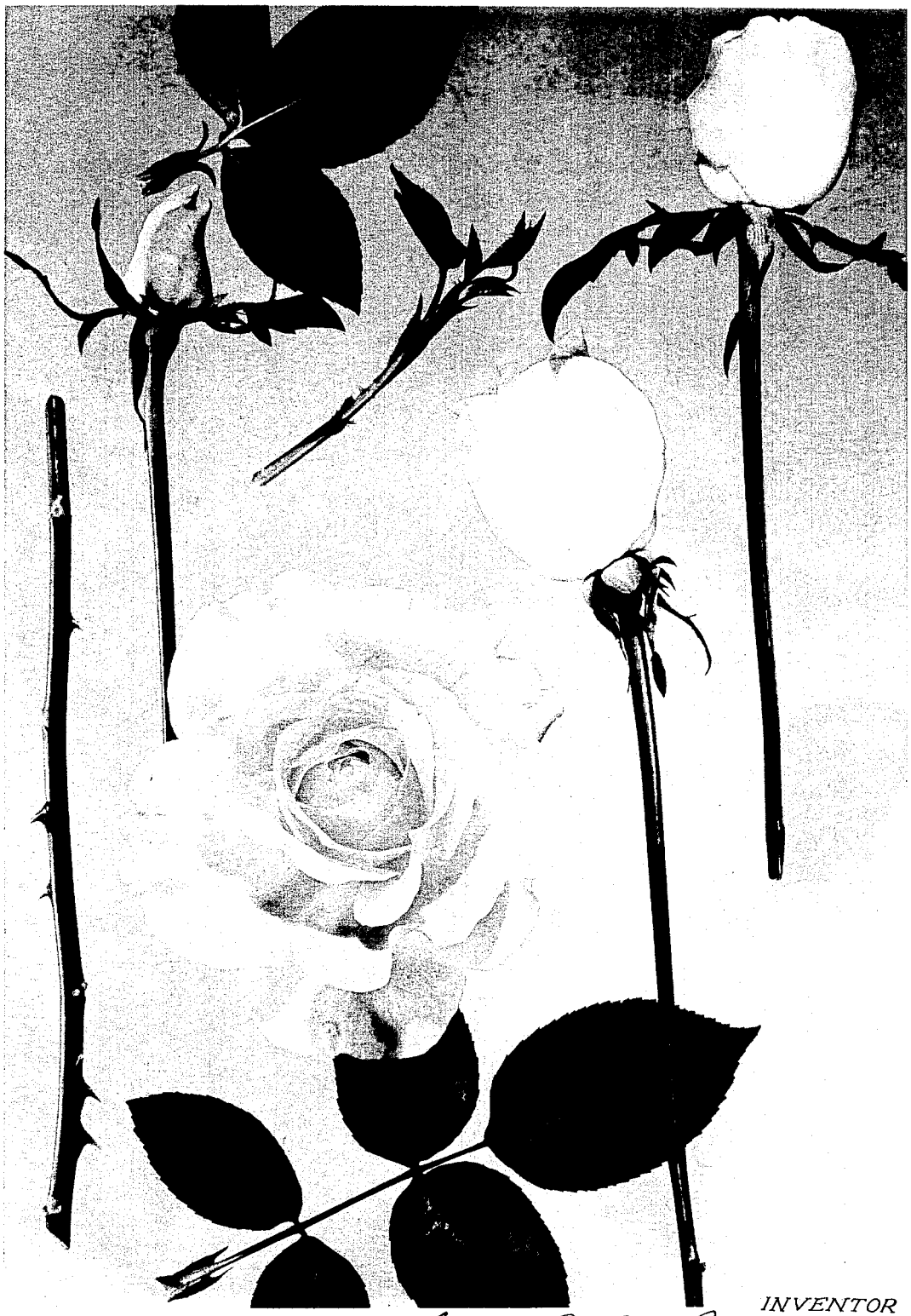
INVENTOR
Sidney Reece and Roy L. Byrum
BY Robbins Robb ATTORNEYS United States Patent Office Plant Pat. 1,774
Patented Nov. 25, 1958

1,774

ROSE PLANT

Sidney Reece and Roy L. Byrum, Richmond, Ind., assignors to Joseph H. Hill Company, Richmond, Ind., a corporation of Indiana Application April 21, 1958, Serial No. 730,030

1 Claim. (Cl. 47—61)

The present invention relates to a new and distinct variety of rose plant of the hybrid tea class, which was discovered by us on property of the assignee of this application by whom we were employed, said new variety having originated as a sport of the variety "Red Better Times," an unpatented sport of the variety "Better Times" (Plant Patent No. 23) identified in the breeding records of our assignee as #47—H H (not to be confused with the red sport of "Better Times" which is the subject of Plant Patent No. 323).

At the time of our initial discovery, we were engaged in cutting blooms from plants of "Red Better Times" which were being grown by our employer in a greenhouse at Richmond, Indiana, and our attention was attracted thereto by the fact that one flower on one plant appeared to be of a distinctly different color from the normal flowers of "Red Better Times." Upon closer observation, we found that one of the plants of "Red Better Times" had sported, and steps were immediately taken to preserve the sport, keep it under close observation, and later to asexually reproduce the same, as performed by budding and grafting at Richmond, Indiana, and also by budding at Wills Point, Texas. These continued observations and reproductions conclusively established that the new sport was definitely differentiated from the parent variety, as well as from all other varieties of which we are aware, particuarly from the standpoint of the color of the flowers which are pink in general color tonality, this color becoming intensified as the flower opens instead of lightening, as is typical of most other forcing pink roses.

While the new sport is comparable in size to the parent variety "Red Better Times," and comparable in form to the variety "Better Times" (Plant Patent No. 23), it is particularly characterized as to novelty by a unique combination of features which has never heretofore been attained in any other variety of which we are aware, the predominant features being as follows:

(1) Absence of "bull-heads";

(2) Absence of malformed flowers;

(3) Absence of "dirty" or cloudy guard petals such as are prevalent in most "Briarcliff" strains;

(4) A distinctive pink general color tonality of the flowers;

(5) An intensification of the flower color as the petals open, contrary to the usual lightening of the color in most forcing pink roses; and (6) Less bluing of the flower color than is typical of most "Briarcliff" strains.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson"), Ridgway's Color Standards and Nomenclature (hereinafter abbreviated as "Ridgway"), and Koster's Color Guide (hereinafter abbreviated as "Koster"), as indicated:

Type: Greenhouse; bush; sport.

Class: Hybrid tea.

Parentage: Sport of "Red Better Times" (unpatented variety #47—H H).

Propagation: Holds its distinguishing characteristics through succeeding propagations by both grafting and budding.

*Flower*

Locality where grown and observed: Richmond, Indiana.

Flowers borne: 1 to a stem; on strong, long stems.

Quantity of bloom: Free, in greenhouse.

Continuity: Continuous.

Fragrance: Strong and penetrating. Nature—tea.

Bud:

*Peduncle.*—Medium length; large; strong; erect. Bark—smooth; color—Scheeles Green, Plate Plate 860/1 (Wilson). Thorns—none. Prickles—none. Hairs—none.

*Before calyx breaks.*—Size—medium large. Form—long pointed; ovoid; with a conspicuous neck; with foliaceous appendages on the surface of the bud; with stout foliaceous parts extending beyond the tip of the bud equal to ¾ or more of its length. Color—Rose Madder, Plate 23/1 (Wilson).

*As calyx breaks.*—Color (outside of petal)—Rose Madder, Plate 23/1 (Wilson), with base of petal Mimosa Yellow, Plate 602/3 (Wilson), and with veins Pod Green, Plate 061/1 (Wilson).

*As first petal opens.*—Size—medium large. Form—long pointed; ovoid. Color: outside—Phlox Pink, Plate 625/2 (Wilson), with base Mimosa Yellow, Plate 602/3 (Wilson); inside—Phlox Pink, Plate 625/3 (Wilson), with tints of Phlox Pink, Plate 625/2 (Wilson), and with base Mimosa Yellow, Plate 602/3 (Wilson).

*Opening.*—Opens up well in greenhouse; no unusual characteristics.

Bloom:

*Size (when fully open).*—Large; from 4 inches to 5 inches.

*Petalage.*—Double (more petals, but the stamens not hidden); from 25 to 35 petals; arranged regularly.

*Form.*—Full and high-centered at first, but becoming open; petals being at first tightly rolled outward, but later becoming loosely rolled outward at maturity.

Petals:

*Texture.*—Moderately thick; leathery. Inside—satiny. Outside—satiny.

*Shape.*—Outer petals—obovate, with apex obtuse. Intermediate petals—obovate, with apex obtuse. Inner petals—obovate, with apex retuse and with one notch.

This description of a newly opened flower was made from a rose grown in a greenhouse in the month of October, at Richmond, Indiana:

*Color.*—Outer petal: outside surface—Phlox Pink, Plate 625/3 (Wilson), with top edge of petal Phlox Pink, Plate 625/2 (Wilson), with base of petal Mimosa Yellow, Plate 602/3 (Wilson), and with veins Pod Green, Plate 061/1 (Wilson); inside surface—Phlox Pink, Plate 625/2 (Wilson), with base from Mimosa Yellow, Plate 602/3 (Wilson) to Mimosa Yellow, Plate 602/2 (Wilson). Intermediate petal: outside surface—Phlox Pink, Plate 625/2 (Wilson), with outside edge Phlox Pink, Plate 625/1 (Wilson), and some having white streak in center, and with base Mimosa Yellow, Plate 602/3 (Wilson); inside surface—Phlox Pink, Plate 625/2 (Wilson), with base from Mimosa Yellow, Plate 602/3 (Wilson) to Mimosa Yellow, Plate 602/2 (Wilson). Inner petal: outside surface—Phlox Pink, Plate 625/1 (Wilson), with edge Phlox Pink, Plate 625 (Wilson), and most having a white streak in center, and with base Mimosa Yellow, Plate 602/2 (Wilson); inside surface—Phlox Pink, Plate 625/1 (Wilson), with edge Phlox Pink, Plate 625 (Wilson), and with base Mimosa Yellow, Plate 602/2 (Wilson).

This description was made from a rose that was open for 3 days in a greenhouse in the month of November, at Richmond, Indiana:

*Color.*—Outer petal: outside surface—Rhodamine Pink, Plate 572/3 (Wilson), with base from Mimosa Yellow, Plate 602/2 (Wilson) to Mimosa Yellow, Plate 602/3 (Wilson); inside surface—Rhodamine Pink, Plate 527/3 (Wilson), with base Mimosa Yellow, Plate 602/3 (Wilson). Intermediate petal: outside surface—Rhodamine Pink, Plate 527/2 (Wilson), with base from Mimosa Yellow, Plate 602/2 (Wilson) to Mimosa Yellow, Plate 602/3 (Wilson), with some having white streak through center of petal; inside surface—Rhodamine Pink, Plate 527/1 (Wilson), with base from Mimosa Yellow, Plate 602/2 (Wilson) to Mimosa Yellow, Plate 602/1 (Wilson). Inner petal: outside surface—Rhodamine Pink, Plate 527 (Wilson), with base Mimosa Yellow, Plate 602/3 (Wilson), with some having white streak through center of petal; inside surface—Rhodamine Pink, Plate 527/1 (Wilson), with base Mimosa Yellow, Plate 602/2 (Wilson), and with some having white streak through center of petal.

*General color effect.*—Newly opened flower—from Phlox Pink, Plate 625/3 (Wilson) to Phlox Pink, Plate 625/2 (Wilson). 3-days open—Rhodamine Pink, Plate 527/1 (Wilson).

*Behavior.*—Persist; no unusual characteristics attributed to weather conditions; fading to shades of from Amaranth Rose, Plate 530 (Wilson), through Amaranth Rose, Plate 530/1 (Wilson) to Amaranth Rose, Plate 530/2 (Wilson).

*Flower longevity.*—Cut roses grown in greenhouse and kept at living-room temperatures—from 4 to 6 days in October.

*Reproductive organs*

Stamens: medium number; arranged irregularly about pistils.

Filaments: Medium length; few without anthers. Color—Mimosa Yellow, Plate 602/3 (Wilson).

Anthers: Medium size; all open at once. Color—Yellow Ochre, Plate 07/1 (Wilson).

Pollen: Sparse. Color—Yellow Ochre, Plate 07/3 (Wilson).

Pistils: Medium number.

Styles: Uneven; medium length; bunched. Color—Pure White, Plate #1 (Koster).

Stigma: Color—Pure White, Plate #1 (Koster).

Ovularies: Some protruding from calyx.

Hips: None developed.

Sepals: Permanent; moderately long; spear-shaped. Color: inside—Pod Green, Plate 061/2 (Wilson), gradually changing through Pod Green, Plate 061/1 (Wilson) and Pod Green, Plate 061 (Wilson) to Spinach Green, Plate 0960 (Wilson) at end; outside—Scheeles Green, Plate 860/1 (Wilson), with a very light touch of Magenta, Plate #50 (Koster) toward end of sepal.

Seeds: None developed.

*Plant*

Foliage:

*Leaves.*—Compound of 5 leaflets; very abundant; large size; heavy; leathery.

*Leaflets.*—Shape—ovoid. Apex—acuminate. Base—round. Margin—simply serrate.

*Color.*—Mature: upper surface—near Parsley Green, Plate 00962 (Wilson), but slightly darker; under surface—near Sage Green, Plate 000861/1 (Wilson), lightly overlaid with Rhodonite Red, Plate 0022/2 (Wilson) on veins. Young: upper surface—Dark Indian Red, Plate XXVII (Ridgway); undersurface—Haematite Red, Plate XXVII (Ridgway).

*Rachis (the supporting stem of the compound leaf).*—Heavy. Upper side—grooved. Under side—prickly.

*Stipules.*—Medium length; medium width; with moderately short points turning out at an angle of less than 45°.

Growth:

*Habit.*—Bush; upright; much-branched.

*Growth.*—Free; vigorous.

*Canes.*—Large diameter.

*Main Stems.*—Color—some Spinach Green, Plate 0960 (Wilson), but others near Maroon, Plate #97 (Koster). Thorns—several; medium length; hooked downward; with short, broad base. Color—Fawn, Plate #89 (Koster). Prickles—none. Hairs—none.

*Branches.*—Color—Scheeles Green, Plate 860/1 (Wilson). Thorns—several; medium length; hooked downward; with long, narrow base; color—Yellow Ochre, Plate 07/3 (Wilson). Prickles—none. Hairs—none.

*New shoots.*—Color—from Scheeles Green, Plate 860/3 (Wilson) to Scheeles Green, Plate 860/2 (Wilson). Thorns—several; medium length; hooked downward; with long, narrow base; color—Amaranth Red, Plate #43 (Koster), with tips changing to Pod Green, Plate 061/3 (Wilson). Prickles—none. Hairs—none.

I claim:

A new and distinct variety of rose plant of the hybrid tea class, substantially as herein shown and described, characterized particularly as to novelty by the unique combination of freedom from "bull-heads," absence of malformed flowers, absence of "dirty" or cloudy guard petals in the flowers, a distinctive pink general color tonality of the flowers, an intensification of the pink flower color as the flowers open, and the absence of substantial "bluing" of the flowers.

No references cited.

Dedication

Plant Pat. No. 1,774.—*Sidney Reece* and *Roy L. Byrum*, Richmond, Ind. ROSE PLANT. Patent dated Nov. 25, 1958. Dedication filed Sept. 21, 1971, by the assignee, *Joseph H. Hill Company*.

Hereby dedicates its entire interest in the said patent to the Public of the United States.

[*Official Gazette November 9, 1971.*]